United States Patent
Michaud et al.

(10) Patent No.: US 11,464,908 B2
(45) Date of Patent: Oct. 11, 2022

(54) METHODS AND APPARATUS FOR MONITORING INFUSION SITES FOR AMBULATORY INFUSION PUMPS

(71) Applicant: Tandem Diabetes Care, Inc., San Diego, CA (US)

(72) Inventors: Michael Michaud, San Diego, CA (US); Geoffrey A. Kruse, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 121 days.

(21) Appl. No.: 16/793,662

(22) Filed: Feb. 18, 2020

(65) Prior Publication Data

US 2020/0261649 A1      Aug. 20, 2020

Related U.S. Application Data

(60) Provisional application No. 62/807,047, filed on Feb. 18, 2019.

(51) Int. Cl.
   *A61M 5/172*      (2006.01)
   *A61M 5/142*      (2006.01)

(52) U.S. Cl.
   CPC ...... *A61M 5/1723* (2013.01); *A61M 5/14248* (2013.01); *A61M 2205/18* (2013.01); *A61M 2205/505* (2013.01); *A61M 2205/52* (2013.01); *A61M 2230/201* (2013.01)

(58) Field of Classification Search
   CPC ........ A61M 5/1723; A61M 2005/1726; A61M 2230/201; A61M 5/16836; A61M 2205/52; A61M 2005/14208; A61M 5/14244; A61M 5/14248; A61M 2230/005; A61M 2205/18; A61M 2205/505
   See application file for complete search history.

(56) References Cited

U.S. PATENT DOCUMENTS

| | | |
|---|---|---|
| 4,403,984 A | 9/1983 | Ash et al. |
| 4,445,885 A | 5/1984 | Kifune |
| 5,299,571 A | 4/1994 | Mastrototaro |

(Continued)

FOREIGN PATENT DOCUMENTS

| | | | | |
|---|---|---|---|---|
| AT | WO 2014122269 A1 * | 8/2014 | ........ | A61M 5/16836 |
| EP | 3319518 A1 | 5/2018 | | |

(Continued)

OTHER PUBLICATIONS

Application and File history for U.S. Appl. No. 13/923,556, filed Jun. 21, 2013, Inventors Rosinko.

(Continued)

*Primary Examiner* — Amber R Stiles
(74) *Attorney, Agent, or Firm* — Patterson Thuente Pedersen, P.A.

(57) ABSTRACT

Disclosed herein are apparatuses and methods for improved use of infusion sites for infusion pumps. Apparatuses and methods for delivery of medicaments such as insulin disclosed herein can increase the effectiveness of therapy by more accurately determining when an infusion site is no longer absorbing insulin at an acceptable rate as well as determining the effectiveness of different infusion sites on the body with respect to each other and over time.

19 Claims, 8 Drawing Sheets

(56) References Cited

U.S. PATENT DOCUMENTS

| | | |
|---|---|---|
| 5,387,327 A | 2/1995 | Khan |
| 5,469,846 A | 11/1995 | Khan |
| 5,527,288 A | 6/1996 | Gross et al. |
| 5,558,638 A | 9/1996 | Evers et al. |
| 5,605,152 A | 2/1997 | Slate et al. |
| 5,741,211 A | 4/1998 | Renirie et al. |
| 5,800,420 A | 9/1998 | Gross et al. |
| 5,807,375 A | 9/1998 | Gross et al. |
| 5,848,991 A | 12/1998 | Gross et al. |
| 5,951,521 A | 9/1999 | Mastrototaro et al. |
| 5,995,860 A | 11/1999 | Sun et al. |
| 5,997,501 A | 12/1999 | Gross et al. |
| 6,017,318 A | 1/2000 | Gauthier et al. |
| 6,122,536 A | 9/2000 | Sun et al. |
| 6,175,752 B1 | 1/2001 | Say et al. |
| 6,256,533 B1 | 7/2001 | Yuzhakov et al. |
| 6,275,717 B1 | 8/2001 | Gross et al. |
| 6,475,750 B1 | 11/2002 | Han et al. |
| 6,558,351 B1 | 5/2003 | Steil et al. |
| 6,565,509 B1 | 5/2003 | Say et al. |
| 6,572,542 B1 | 6/2003 | Houben et al. |
| 6,577,899 B2 | 6/2003 | Lebel et al. |
| 6,585,644 B2 | 7/2003 | Lebel et al. |
| 6,623,698 B2 | 9/2003 | Kuo |
| 6,668,196 B1 | 12/2003 | Villegas et al. |
| 6,669,663 B1 | 12/2003 | Thompson |
| 6,731,976 B2 | 5/2004 | Penn et al. |
| 6,740,072 B2 | 5/2004 | Starkweather et al. |
| 6,740,075 B2 | 5/2004 | Lebel et al. |
| 6,758,810 B2 | 7/2004 | Lebel et al. |
| 6,810,290 B2 | 10/2004 | Lebel et al. |
| 7,198,603 B2 | 4/2007 | Penner et al. |
| 7,267,665 B2 | 9/2007 | Steil et al. |
| 7,278,983 B2 | 10/2007 | Ireland et al. |
| 7,320,675 B2 | 1/2008 | Pastore et al. |
| 7,354,420 B2 | 4/2008 | Steil et al. |
| 7,399,401 B2 | 7/2008 | Rush |
| 7,402,153 B2 | 7/2008 | Steil et al. |
| 7,429,255 B2 | 9/2008 | Thompson |
| 7,481,776 B2 | 1/2009 | Boecker et al. |
| 7,491,178 B2 | 2/2009 | Boecker et al. |
| 7,491,187 B2 | 2/2009 | Van Den Berghe et al. |
| 7,497,827 B2 | 3/2009 | Brister et al. |
| 7,515,060 B2 | 4/2009 | Blomquist |
| 7,517,440 B2 | 4/2009 | Anex et al. |
| 7,547,281 B2 | 6/2009 | Hayes et al. |
| 7,563,232 B2 | 7/2009 | Freeman et al. |
| 7,582,099 B2 | 9/2009 | Freeman et al. |
| 7,591,801 B2 | 9/2009 | Brauker et al. |
| 7,594,889 B2 | 9/2009 | St. Ores et al. |
| 7,604,593 B2 | 10/2009 | Parris et al. |
| 7,615,007 B2 | 11/2009 | Shults et al. |
| 7,704,227 B2 | 4/2010 | Moberg et al. |
| 7,715,893 B2 | 5/2010 | Kamath et al. |
| 7,717,903 B2 | 5/2010 | Estes et al. |
| 7,768,408 B2 | 8/2010 | Reggiardo et al. |
| 7,774,145 B2 | 8/2010 | Brauker et al. |
| 7,785,313 B2 | 8/2010 | Mastrototaro |
| 7,806,854 B2 | 10/2010 | Damiano et al. |
| 7,806,886 B2 | 10/2010 | Kanderian, Jr. et al. |
| 7,860,544 B2 | 12/2010 | Say et al. |
| 7,882,611 B2 | 2/2011 | Shah et al. |
| 7,884,729 B2 | 2/2011 | Reggiardo et al. |
| 7,890,295 B2 | 2/2011 | Shin et al. |
| 7,901,394 B2 | 3/2011 | Ireland et al. |
| 7,914,742 B2 | 3/2011 | Arbogast et al. |
| 7,917,186 B2 | 3/2011 | Kamath et al. |
| 7,931,592 B2 | 4/2011 | Currie et al. |
| 7,935,076 B2 | 5/2011 | Estes et al. |
| 7,938,797 B2 | 5/2011 | Estes |
| 7,942,844 B2 | 5/2011 | Moberg et al. |
| 7,946,985 B2 | 5/2011 | Mastrototaro et al. |
| 7,959,598 B2 | 6/2011 | Estes |
| 7,970,620 B2 | 6/2011 | Brown |
| 7,986,986 B2 | 7/2011 | Goode et al. |
| 7,988,630 B1 | 8/2011 | Osorio et al. |
| 7,998,110 B2 | 8/2011 | Leung et al. |
| 8,016,783 B2 | 9/2011 | Pastore et al. |
| 8,021,299 B2 | 9/2011 | Miesel et al. |
| 8,029,459 B2 | 10/2011 | Rush et al. |
| 8,062,249 B2 | 11/2011 | Wilinska et al. |
| 8,095,197 B2 | 1/2012 | Santini, Jr. et al. |
| 8,100,852 B2 | 1/2012 | Moberg et al. |
| 8,109,921 B2 | 2/2012 | Estes et al. |
| 8,114,023 B2 | 2/2012 | Ward et al. |
| 8,121,857 B2 | 2/2012 | Galasso et al. |
| 8,126,728 B2 | 2/2012 | Dicks et al. |
| 8,126,729 B2 | 2/2012 | Dicks et al. |
| 8,126,730 B2 | 2/2012 | Dicks et al. |
| 8,126,732 B2 | 2/2012 | Dicks et al. |
| 8,126,733 B2 | 2/2012 | Dicks et al. |
| 8,126,734 B2 | 2/2012 | Dicks et al. |
| 8,140,356 B2 | 3/2012 | Dicks et al. |
| 8,155,982 B2 | 4/2012 | Dicks et al. |
| 8,221,385 B2 | 7/2012 | Estes |
| 8,257,300 B2 | 9/2012 | Budiman et al. |
| 8,275,438 B2 | 9/2012 | Simpson |
| 8,277,435 B2 | 10/2012 | Estes |
| 8,287,487 B2 | 10/2012 | Estes |
| 8,287,495 B2 | 10/2012 | Michaud et al. |
| 8,298,184 B2 | 10/2012 | DiPerna et al. |
| 8,323,188 B2 | 12/2012 | Tran |
| 8,328,754 B2 | 12/2012 | Estes et al. |
| 8,343,092 B2 | 1/2013 | Rush et al. |
| 8,344,847 B2 | 1/2013 | Moberg et al. |
| 8,348,885 B2 | 1/2013 | Moberg et al. |
| 8,348,886 B2 | 1/2013 | Kanderian, Jr. et al. |
| 8,348,923 B2 | 1/2013 | Kanderian, Jr. et al. |
| 8,353,881 B2 | 1/2013 | Jennewine |
| 8,357,091 B2 | 1/2013 | Say et al. |
| 8,369,919 B2 | 2/2013 | Kamath et al. |
| 8,372,351 B2 | 2/2013 | Ow-Wing |
| 8,454,576 B2 | 6/2013 | Mastrototaro et al. |
| 8,460,231 B2 | 6/2013 | Brauker et al. |
| 8,461,985 B2 | 6/2013 | Fennell et al. |
| 8,512,276 B2 | 8/2013 | Talbot |
| 8,573,027 B2 | 11/2013 | Rosinko et al. |
| 8,635,085 B2 | 1/2014 | Brown |
| 8,650,937 B2 | 2/2014 | Brown |
| 8,663,201 B2 | 3/2014 | Hill |
| 8,986,253 B2 | 3/2015 | DiPerna |
| 9,037,254 B2 | 5/2015 | John |
| 9,089,305 B2 | 7/2015 | Hovorka |
| 9,114,210 B2 | 8/2015 | Estes |
| 9,259,175 B2 | 2/2016 | Stafford |
| 9,277,010 B2 | 3/2016 | Venkatesh et al. |
| 9,326,709 B2 | 5/2016 | Budiman |
| 9,364,679 B2 | 6/2016 | John |
| 9,381,297 B2 | 7/2016 | Brown et al. |
| 9,486,171 B2 | 11/2016 | Saint |
| 9,555,186 B2 | 1/2017 | Kruse |
| 9,669,160 B2 | 6/2017 | Harris |
| 9,833,177 B2 | 12/2017 | Blomquist |
| 9,844,627 B2 | 12/2017 | Estes |
| 9,867,937 B2 | 1/2018 | Saint et al. |
| 9,867,953 B2 | 1/2018 | Rosinko |
| 9,974,903 B1 | 5/2018 | Davis |
| 9,993,595 B2 | 6/2018 | Michaud et al. |
| 10,016,561 B2 | 7/2018 | Saint et al. |
| 10,052,049 B2 | 8/2018 | Blomquist et al. |
| 10,213,547 B2 | 2/2019 | Rosinko |
| 10,279,105 B2 | 5/2019 | Rosinko |
| 10,279,106 B1 | 5/2019 | Cook et al. |
| 10,279,107 B2 | 5/2019 | Michaud |
| 10,357,606 B2 | 7/2019 | Rosinko et al. |
| 10,357,607 B2 | 7/2019 | Rosinko et al. |
| 10,549,051 B2 | 2/2020 | Rosinko |
| 10,569,016 B2 | 2/2020 | Rosinko |
| 10,864,322 B2 | 12/2020 | Saint et al. |
| 2002/0198483 A1 | 12/2002 | Wariar et al. |
| 2003/0055406 A1 | 3/2003 | Lebel |
| 2003/0060765 A1 | 3/2003 | Campbell et al. |
| 2003/0065308 A1 | 4/2003 | Lebel et al. |
| 2003/0130616 A1 | 7/2003 | Steil |

(56) References Cited

U.S. PATENT DOCUMENTS

| | | |
|---|---|---|
| 2003/0212379 A1 | 11/2003 | Bylund |
| 2004/0068230 A1 | 4/2004 | Estes et al. |
| 2004/0122353 A1 | 6/2004 | Shahmirian et al. |
| 2004/0152622 A1 | 8/2004 | Keith et al. |
| 2004/0167464 A1 | 8/2004 | Ireland |
| 2004/0193025 A1 | 9/2004 | Steil |
| 2004/0193090 A1 | 9/2004 | Lebel et al. |
| 2005/0038325 A1 | 2/2005 | Moll |
| 2005/0171503 A1 | 2/2005 | Berghe |
| 2005/0065464 A1 | 3/2005 | Talbot et al. |
| 2005/0137530 A1 | 6/2005 | Campbell et al. |
| 2005/0192557 A1 | 9/2005 | Brauker |
| 2005/0272640 A1 | 12/2005 | Doyle |
| 2005/0272989 A1 | 12/2005 | Shah et al. |
| 2006/0031094 A1 | 2/2006 | Cohen et al. |
| 2006/0089542 A1 | 4/2006 | Sands |
| 2006/0130591 A1 | 6/2006 | Perkins |
| 2006/0224109 A1 | 10/2006 | Steil |
| 2006/0224141 A1 | 10/2006 | Rush et al. |
| 2007/0033074 A1 | 2/2007 | Nitzan et al. |
| 2007/0060869 A1 | 3/2007 | Tolle et al. |
| 2007/0093786 A1 | 4/2007 | Goldsmith et al. |
| 2007/0100222 A1 | 5/2007 | Mastrototaro et al. |
| 2007/0173761 A1 | 7/2007 | Kanderian |
| 2007/0227907 A1 | 10/2007 | Shah et al. |
| 2007/0251835 A1 | 11/2007 | Mehta et al. |
| 2007/0253021 A1 | 11/2007 | Mehta et al. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255126 A1 | 11/2007 | Moberg et al. |
| 2007/0255348 A1 | 11/2007 | Holtzclaw |
| 2007/0258395 A1 | 11/2007 | Jollota et al. |
| 2007/0293843 A1 | 12/2007 | Ireland |
| 2008/0065006 A1 | 3/2008 | Roger et al. |
| 2008/0071580 A1 | 3/2008 | Marcus et al. |
| 2008/0097246 A1 | 4/2008 | Stafford |
| 2008/0097917 A1 | 4/2008 | Dicks et al. |
| 2008/0103554 A1 | 5/2008 | Dicks et al. |
| 2008/0114228 A1 | 5/2008 | McCluskey et al. |
| 2008/0119707 A1 | 5/2008 | Stafford |
| 2008/0125700 A1 | 5/2008 | Moberg et al. |
| 2008/0125701 A1 | 5/2008 | Moberg |
| 2008/0139910 A1 | 6/2008 | Mastrototaro et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0195060 A1 | 8/2008 | Roger et al. |
| 2008/0228056 A1 | 9/2008 | Blomquist et al. |
| 2008/0269714 A1 | 10/2008 | Mastrototaro et al. |
| 2008/0269723 A1 | 10/2008 | Mastrototaro et al. |
| 2008/0281297 A1 | 11/2008 | Pesach |
| 2008/0300572 A1 | 12/2008 | Rankers et al. |
| 2009/0005724 A1 | 1/2009 | Regittnig et al. |
| 2009/0062767 A1 | 3/2009 | Van et al. |
| 2009/0069745 A1 | 3/2009 | Estes et al. |
| 2009/0069787 A1 | 3/2009 | Estes et al. |
| 2009/0082647 A1 | 3/2009 | Busby |
| 2009/0082653 A1 | 3/2009 | Rohde |
| 2009/0088731 A1 | 4/2009 | Campbell et al. |
| 2009/0105636 A1 | 4/2009 | Hayter et al. |
| 2009/0112626 A1 | 4/2009 | Talbot et al. |
| 2009/0113295 A1 | 4/2009 | Halpern et al. |
| 2009/0163855 A1 | 6/2009 | Shin et al. |
| 2009/0192724 A1 | 7/2009 | Brauker et al. |
| 2009/0192745 A1 | 7/2009 | Kamath et al. |
| 2009/0221890 A1 | 9/2009 | Saffer et al. |
| 2009/0227855 A1 | 9/2009 | Hill et al. |
| 2009/0240193 A1 | 9/2009 | Mensinger et al. |
| 2009/0254037 A1 | 10/2009 | Bryant, Jr. et al. |
| 2009/0275887 A1 | 11/2009 | Estes |
| 2009/0281393 A1 | 11/2009 | Smith |
| 2010/0010330 A1 | 1/2010 | Rankers et al. |
| 2010/0030045 A1 | 2/2010 | Gottlieb et al. |
| 2010/0030092 A1 | 2/2010 | Kristensen et al. |
| 2010/0049164 A1 | 2/2010 | Estes |
| 2010/0057040 A1 | 3/2010 | Hayter |
| 2010/0076412 A1 | 3/2010 | Rush et al. |
| 2010/0094251 A1 | 4/2010 | Estes |
| 2010/0114015 A1 | 5/2010 | Kanderian, Jr. et al. |
| 2010/0121169 A1 | 5/2010 | Petisce et al. |
| 2010/0168538 A1 | 7/2010 | Keenan et al. |
| 2010/0174266 A1 | 7/2010 | Estes |
| 2010/0198034 A1 | 8/2010 | Thomas et al. |
| 2010/0228186 A1 | 9/2010 | Estes et al. |
| 2010/0261987 A1 | 10/2010 | Kamath et al. |
| 2010/0274218 A1 | 10/2010 | Yodfat et al. |
| 2010/0274592 A1 | 10/2010 | Nitzan et al. |
| 2010/0292556 A1 | 11/2010 | Golden |
| 2010/0298681 A1 | 11/2010 | Say et al. |
| 2010/0305421 A1 | 12/2010 | Ow-Wing |
| 2010/0305545 A1 | 12/2010 | Kanderian, Jr. et al. |
| 2010/0324382 A1 | 12/2010 | Cantwell et al. |
| 2010/0324392 A1 | 12/2010 | Yee |
| 2011/0006876 A1 | 1/2011 | Moberg et al. |
| 2011/0009725 A1 | 1/2011 | Hill et al. |
| 2011/0009813 A1 | 1/2011 | Rankers |
| 2011/0015509 A1 | 1/2011 | Peyser |
| 2011/0040247 A1 | 2/2011 | Mandro et al. |
| 2011/0047499 A1 | 2/2011 | Mandro et al. |
| 2011/0050428 A1 | 3/2011 | Istoc |
| 2011/0053121 A1 | 3/2011 | Heaton |
| 2011/0054391 A1 | 3/2011 | Ward et al. |
| 2011/0071464 A1 | 3/2011 | Palerm |
| 2011/0078441 A1 | 3/2011 | Dicks et al. |
| 2011/0093285 A1 | 4/2011 | Dicks et al. |
| 2011/0093286 A1 | 4/2011 | Dicks et al. |
| 2011/0105873 A1 | 5/2011 | Feldman et al. |
| 2011/0105955 A1 | 5/2011 | Yudovsky et al. |
| 2011/0106011 A1 | 5/2011 | Cinar et al. |
| 2011/0106049 A1 | 5/2011 | Damiano et al. |
| 2011/0124999 A1 | 5/2011 | Reggiardo et al. |
| 2011/0130746 A1 | 6/2011 | Budiman |
| 2011/0144586 A1 | 6/2011 | Michaud et al. |
| 2011/0144616 A1 | 6/2011 | Michaud et al. |
| 2011/0152653 A1 | 6/2011 | Shekalim et al. |
| 2011/0152770 A1 | 6/2011 | DiPerna et al. |
| 2011/0152824 A1 | 6/2011 | DiPerna et al. |
| 2011/0166544 A1 | 7/2011 | Verhoef et al. |
| 2011/0178462 A1 | 7/2011 | Moberg et al. |
| 2011/0184342 A1 | 7/2011 | Pesach et al. |
| 2011/0193704 A1 | 8/2011 | Harper et al. |
| 2011/0201911 A1 | 8/2011 | Johnson |
| 2011/0208155 A1 | 8/2011 | Palerm et al. |
| 2011/0213225 A1 | 9/2011 | Bernstein et al. |
| 2011/0257627 A1 | 10/2011 | Hovorka |
| 2012/0029433 A1 | 2/2012 | Michaud et al. |
| 2012/0030610 A1 | 2/2012 | DiPerna et al. |
| 2012/0053522 A1 | 3/2012 | Yodfat et al. |
| 2012/0078067 A1 | 3/2012 | Kovatchev |
| 2012/0116197 A1 | 5/2012 | Moberg |
| 2012/0123230 A1 | 5/2012 | Brown et al. |
| 2012/0191052 A1 | 7/2012 | Rao |
| 2012/0277667 A1 | 11/2012 | Yodat et al. |
| 2012/0330227 A1 | 12/2012 | Budiman et al. |
| 2013/0053816 A1 | 2/2013 | DiPerna et al. |
| 2013/0237955 A1 | 9/2013 | Neta et al. |
| 2013/0324928 A1 | 12/2013 | Kruse |
| 2014/0005633 A1 | 1/2014 | Finan |
| 2014/0137641 A1 | 5/2014 | Brown |
| 2014/0171772 A1 | 6/2014 | Blomquist |
| 2014/0180203 A1 | 6/2014 | Budiman |
| 2014/0187890 A1 | 7/2014 | Mensinger |
| 2014/0200426 A1 | 7/2014 | Taub |
| 2014/0273042 A1 | 9/2014 | Saint |
| 2014/0276419 A1 | 9/2014 | Rosinko et al. |
| 2014/0276423 A1 | 9/2014 | Lecanu-Fayet |
| 2014/0276556 A1 | 9/2014 | Saint et al. |
| 2014/0350371 A1 | 11/2014 | Blomquist et al. |

(56) References Cited

U.S. PATENT DOCUMENTS

| | | |
|---|---|---|
| 2015/0073337 A1 | 3/2015 | Saint et al. |
| 2015/0151082 A1 | 6/2015 | Gescheit |
| 2015/0182693 A1 | 7/2015 | Rosinko |
| 2016/0030669 A1 | 2/2016 | Harris et al. |
| 2016/0082188 A1 | 3/2016 | Blomquist et al. |
| 2016/0199571 A1 | 7/2016 | Rosinko et al. |
| 2017/0000943 A1 | 1/2017 | Blomquist et al. |
| 2017/0035962 A1 | 2/2017 | Lecanu-Fayet et al. |
| 2018/0071454 A1 | 3/2018 | Betts et al. |
| 2018/0092578 A1 | 4/2018 | Blomquist |
| 2018/0093039 A1 | 4/2018 | Estes |
| 2018/0161498 A1 | 6/2018 | Estes |
| 2018/0177946 A1 * | 6/2018 | Loutseiko .............. G16H 20/17 |
| 2019/0022314 A1 | 1/2019 | Schmidt |
| 2019/0328967 A1 | 10/2019 | Rosinko et al. |
| 2019/0350501 A1 | 11/2019 | Blomquist et al. |
| 2019/0365997 A1 | 12/2019 | Harris |
| 2019/0388015 A1 | 12/2019 | Blomquist |
| 2020/0101224 A1 | 4/2020 | Lintereur |
| 2020/0101226 A1 | 4/2020 | Saint et al. |
| 2020/0114076 A1 | 4/2020 | Ulrich et al. |
| 2020/0171249 A1 | 6/2020 | Rosinko |

FOREIGN PATENT DOCUMENTS

| | | | |
|---|---|---|---|
| IL | WO 2011039741 A1 * | 4/2011 | .. A61M 2005/14208 |
| WO | WO-9528878 A1 | 11/1995 | |
| WO | WO-2007149533 A2 | 12/2007 | |
| WO | WO-2009032400 A1 | 3/2009 | |
| WO | WO-2009035759 A1 | 3/2009 | |
| WO | WO-2009147680 A2 | 12/2009 | |
| WO | WO2010033878 A2 | 3/2010 | |
| WO | WO-2011014704 A2 | 2/2011 | |
| WO | WO2013184896 A1 | 12/2013 | |
| WO | WO-2018085600 A1 | 5/2018 | |

OTHER PUBLICATIONS

Application and File history for U.S. Appl. No. 15/871,665, filed Jan. 15, 2018, Inventors Rosinko.

Application and File history for U.S. Appl. No. 16/781,051, filed Feb. 4, 2020, Inventors Rosinko.

* cited by examiner

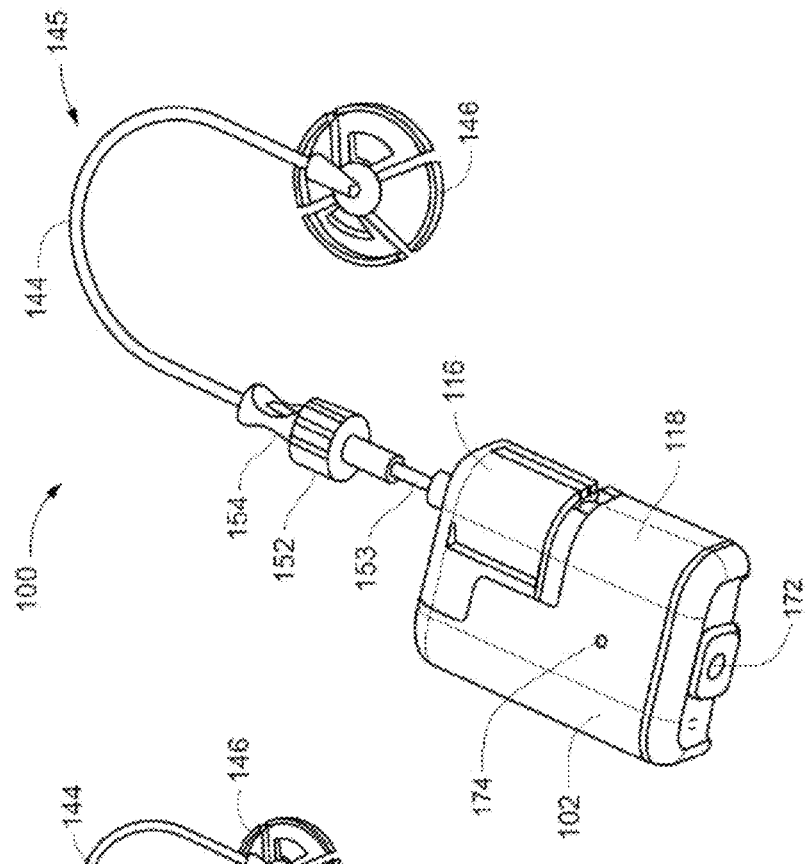
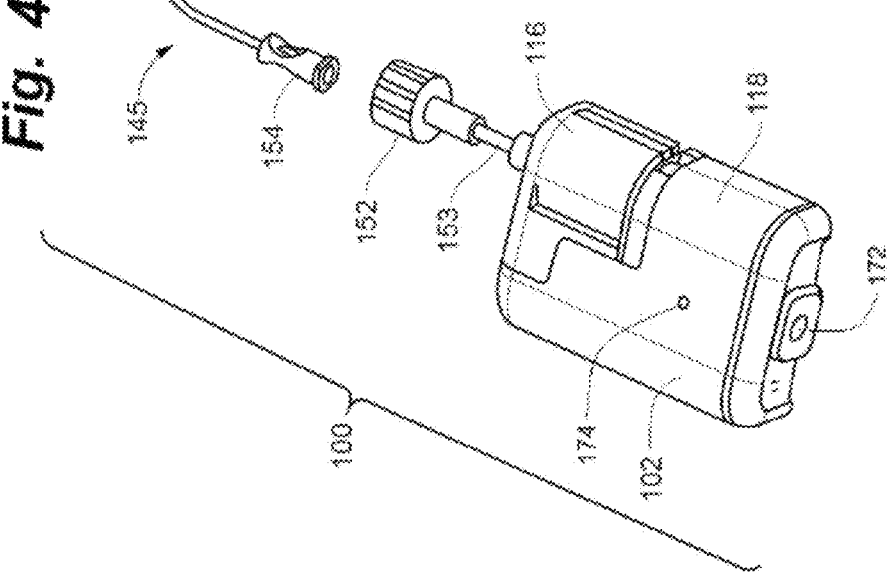

METHODS AND APPARATUS FOR MONITORING INFUSION SITES FOR AMBULATORY INFUSION PUMPS

RELATED APPLICATION

The present application claims the benefit of U.S. Provisional Application No. 62/807,047 filed Feb. 18, 2019, which is hereby incorporated herein in its entirety by reference.

FIELD OF THE INVENTION

The present invention relates to ambulatory infusions pumps and, more particularly, to monitoring of infusion sites used to inject medicament into the body with ambulatory infusion pumps.

BACKGROUND

There are a wide variety of medical treatments that include the administration of a therapeutic fluid in precise, known amounts at predetermined intervals. Devices and methods exist that are directed to the delivery of such fluids, which may be liquids or gases, are known in the art.

One category of such fluid delivery devices includes insulin injecting pumps developed for administering insulin to patients afflicted with type I, or in some cases, type II diabetes. Some insulin injecting pumps are configured as portable or ambulatory infusion devices can provide continuous subcutaneous insulin injection and/or infusion therapy as an alternative to multiple daily injections of insulin via a syringe or an insulin pen. Such pumps are worn by the user and may use replaceable cartridges. In some embodiments, these pumps may also deliver medicaments other than, or in addition to, insulin, such as glucagon, pramlintide, and the like. Examples of such pumps and various features associated therewith include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

Some portable infusion pumps deliver medicament to patients through infusion sets that include tubing extending from the pump and a cannula with an associated needle that penetrates the patient's skin at an infusion site to allow infusion of the medicament through the cannula and into the patient. Some portable infusion pumps that can be worn on the body alternatively or additionally insert a cannula directly beneath the pump into the body. If a patient leaves the needle injected at the injection site for too long a period of time, unwanted side effects such as infection and the accumulation of fat and scar tissue can result. Therefore, patients are often instructed to rotate infusion sites to avoid or minimize side effects. Depending on the type of cannula used, the general physiological response of the patient with regard to insulin absorption, and other factors, the time needed between insulin site rotations can vary. Often, sites are rotated every 24-48 hours or every 48-72 hours. However, not all patients' bodies react the same to infusion therapy and not all infusion locations on a given patient will react the same. A standardized site rotation for all patients at a set amount of time therefore risks both instructing site rotation while a given site is still functional and leaving a site in use when it is no longer working properly.

SUMMARY OF THE INVENTION

Disclosed herein are apparatuses and methods for improved use of infusion sites for infusion pumps. Apparatuses and methods for delivery of medicaments such as insulin disclosed herein can increase the effectiveness of therapy by more accurately determining when an infusion site is no longer absorbing insulin at an acceptable rate as well as determining the effectiveness of different infusion sites on the body with respect to each other and over time.

In embodiments, a system can monitor glucose values over time while an infusion set is in use. The glucose values can be monitored with respect to the amount of medicament delivered to determine if the body is responding as expected to the medicament. If the body is not responding as expected, such as by the glucose levels not lowering an expected amount based on an amount of insulin delivered, an alert can be provided notifying the user that the infusion site is no longer functioning as desired and instructing the user to rotate the infusion set to a new infusion site.

In an embodiment, a method of providing diabetes therapy to a patient with a portable infusion pump can be provided that includes detecting insertion by a patient of a cannula for delivery of medicament with the portable infusion pump at an infusion site on a body of the patient and delivery of medicament to the patient at the infusion site with the portable infusion pump. Data obtained by a glucose sensor can be received and glucose levels of the patient based on the data obtained by the glucose sensor can be monitored to determine if the monitored glucose levels are lowering as expected in response to the medicament being delivered to the patient. An infusion site alert can be provided to the patient if it is determined that the monitored glucose levels are not lowering as expected in response to the medicament.

In embodiments, a user can be provided with the ability and/or instructed to enter a location on the body of an infusion site when a new infusion site is put into use. User entry can include one or more of a text entry indicating an infusion site, selection from a list of infusion sites, and/or selection of a region of the body from a graphical depiction of the body. The system can track and store various parameters during use of the infusion site including, for example, glucose levels and medicament delivery parameters, and store historical data relating to a plurality of infusion sites. The historical data can later be used to compare infusion site performance and/or to provide recommendations for particular infusion sites to use when the infusion site needs to be rotated.

In an embodiment, a method of providing diabetes therapy to a patient with a portable infusion pump can be provided that includes receiving user input indicating a location on a body of a patient being used as an infusion site for delivering medicament to the patient with a portable infusion pump and delivering the medicament to the patient at the infusion site with the portable infusion pump. Data obtained by a glucose sensor can be received and medicament delivery parameters and glucose levels of the patient based on the data obtained by the glucose sensor while medicament is being delivered at the infusion site can be tracked. The tracked medicament delivery parameters and glucose levels while the medicament is being delivered at the infusion site can be stored as a measure of an effectiveness of the infusion site.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 4A-4B depict an embodiment of a pump system according to the disclosure.

Figure 1:
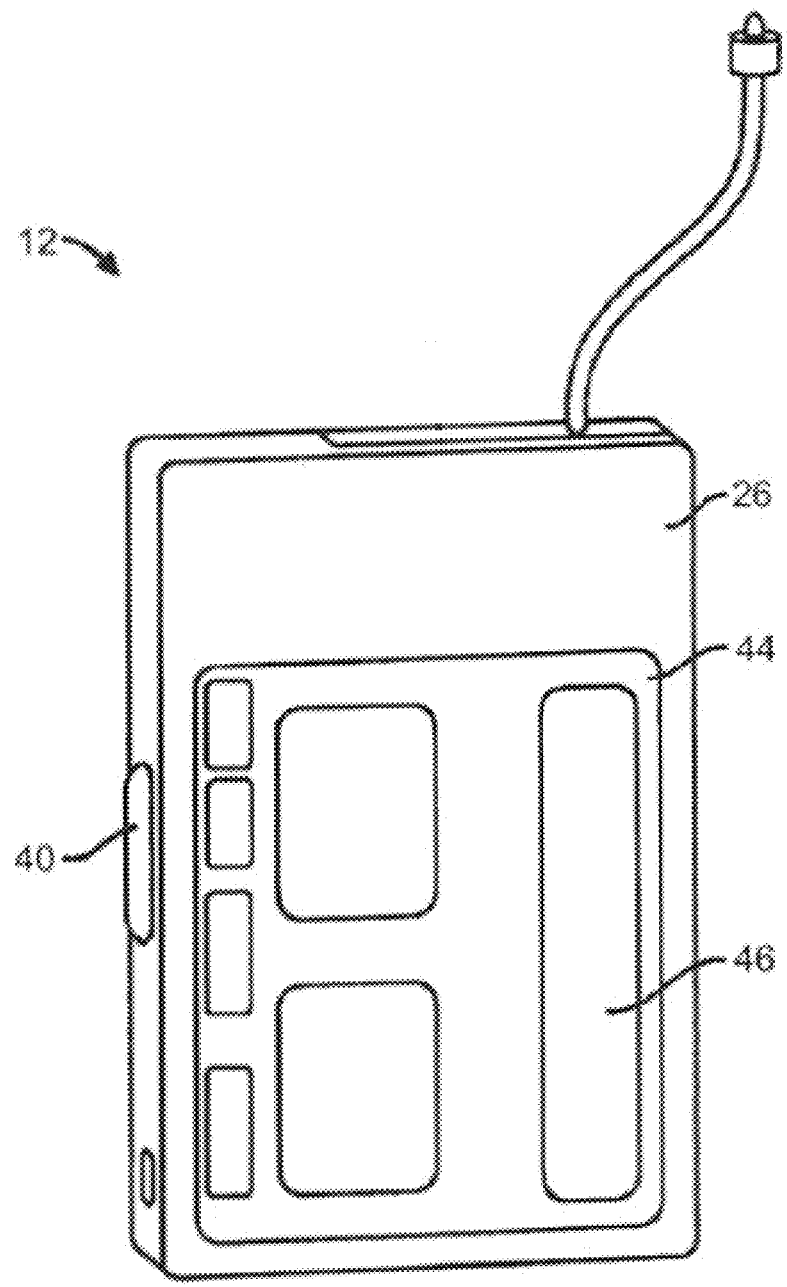
FIG. 1 depicts an embodiment of a pump system according to the disclosure.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

FIG. 1 depicts an exemplary medical device that can be used with embodiments of the disclosure. In this embodiment, the medical device is configured as a pump 12, such as an infusion pump, that can include a pumping or delivery mechanism and reservoir for delivering medicament to a patient and an output/display 44. The type of output/display 44 may vary as may be useful for a particular application. The output/display 44 may include an interactive and/or touch sensitive screen 46 having an input device such as, for example, a touch screen comprising a capacitive screen or a resistive screen. The pump 12 may additionally include a keyboard, microphone, or other input device known in the art for data entry, which may be separate from the display. The pump 12 may also include a capability to operatively couple to one or more blood glucose meters (BGMs) or continuous blood glucose monitors (CGMs) and/or one or more secondary display devices such as a remote display, a remote control device, a laptop computer, personal computer, tablet computer, a mobile communication device such as a smartphone, a wearable electronic watch or electronic health or fitness monitor, or personal digital assistant (PDA), a CGM display etc.

In one embodiment, the medical device can be a portable pump configured to deliver insulin to a patient. Further details regarding such pump devices can be found in U.S. Pat. No. 8,287,495, which is incorporated herein by reference in its entirety. In other embodiments, the medical device can be an infusion pump configured to deliver one or more additional or other medicaments to a patient.

Figure 2:
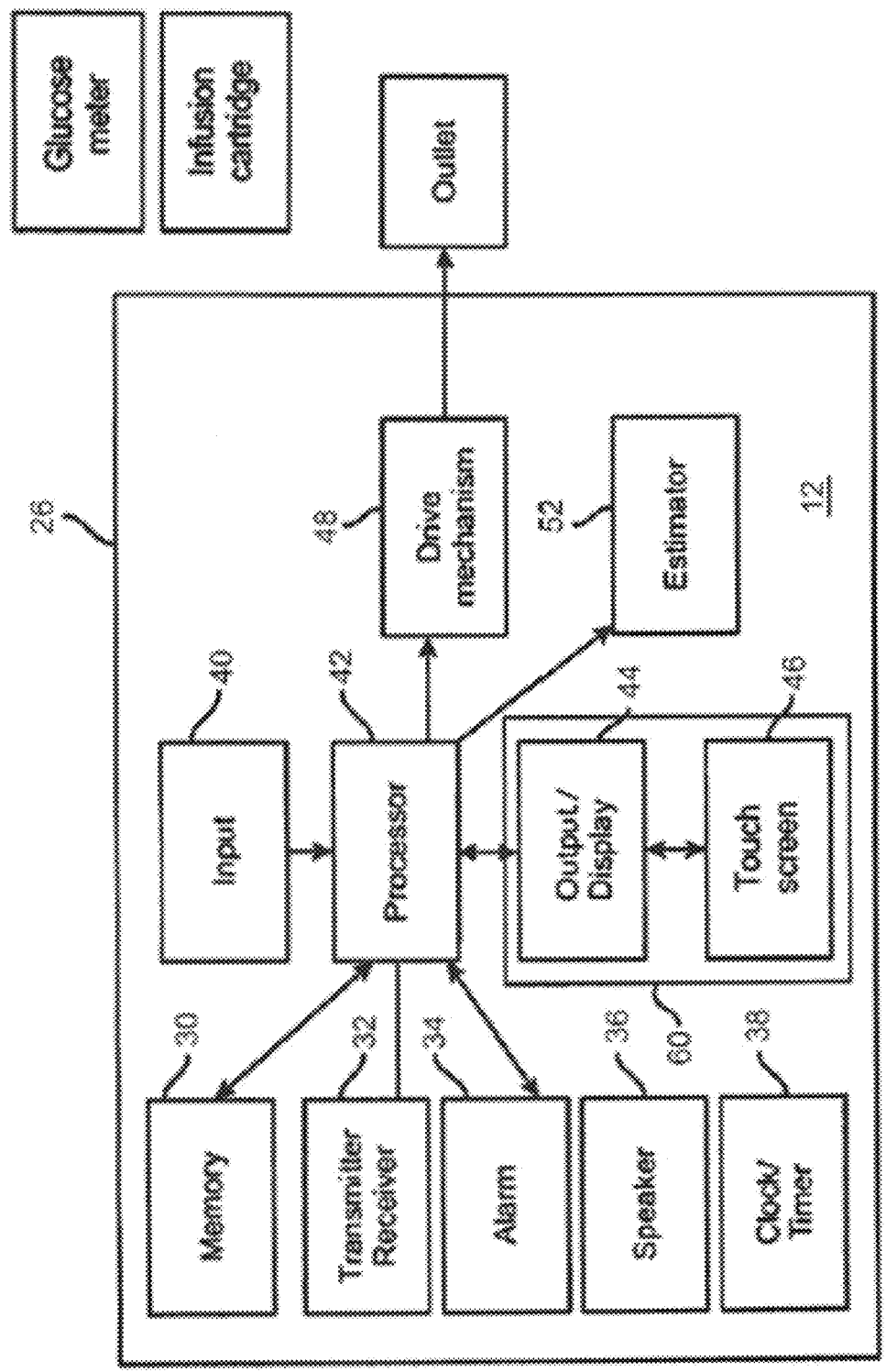
FIG. 2 depicts a block diagram representing an embodiment of a pump system according to the disclosure.

FIG. 2 illustrates a block diagram of some of the features that can be used with embodiments, including features that may be incorporated within the housing 26 of a medical device such as a pump 12. The pump 12 can include a processor 42 that controls the overall functions of the device. The infusion pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface as shown in FIG. 2 is a graphical user interface (GUI) 60 having a touch sensitive screen 46 with input capability. In some embodiments, the processor 42 may communicate with one or more other processors within the pump 12 and/or one or more processors of other devices, for example, a continuous glucose monitor (CGM), display device, smartphone, etc. through the transmitter/receiver. The processor 42 may also include programming that may allow the processor to receive signals and/or other data from one or more input devices, such as sensors that may sense pressure, temperature and/or other parameters.

Figure 3A:
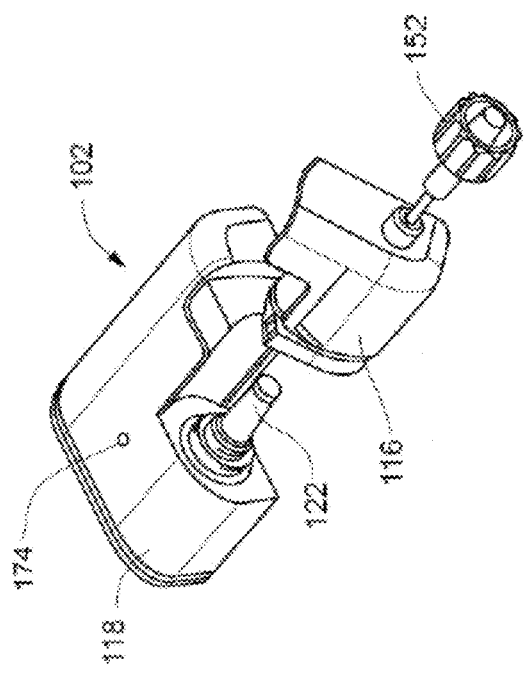
FIGS. 3A-3C depicts an embodiment of a pump system according to the disclosure.
Figure 3B:
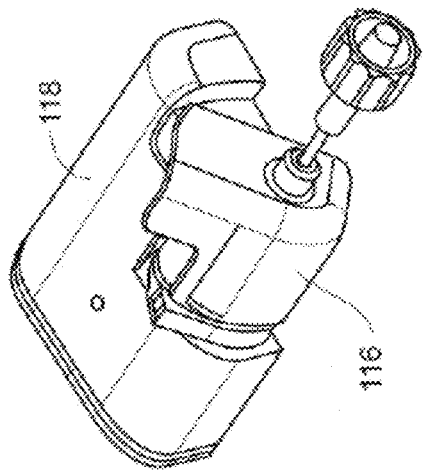
Figure 3C:
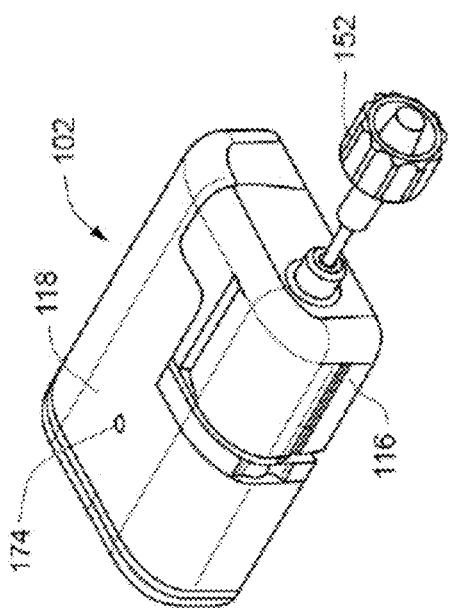

FIGS. 3A-3C depict another pump system including a pump 102 that can be used with embodiments. Drive unit 118 of pump 102 includes a drive mechanism 122 that mates with a recess in disposable cartridge 116 of pump 102 to attach the cartridge 116 to the drive unit 118 and provide for delivery of medicament such as insulin from the cartridge 116 to a user through a cannula. Further details regarding such pumps can be found in U.S. Pat. Nos. 9,993,595, 10,279,106 and 10,279,107, each of which is hereby incorporated herein by reference in its entirety.

In one embodiment, pump 102 includes a processor that controls operations of the pump and, in some embodiments, may receive commands from a separate device for control of operations of the pump. Such a separate device can include, for example, a dedicated remote control or a smartphone or other consumer electronic device executing an application configured to enable the device to transmit operating commands to the processor of pump 102. In some embodiments, processor can also transmit information to one or more separate devices, such as information pertaining to device parameters, alarms, reminders, pump status, etc. In one embodiment pump 102 does not include a display but may include one or more indicator lights 174 and/or one or more input buttons 172. Pump 102 can also incorporate any or all of the features described with respect to pump 12 in FIG. 2.

In one embodiment, pump system 100 can include a short length of tubing 153 and a connector 152. Connector 152 can be configured to attach to a corresponding connector of an infusion set that includes, e.g., a length of tubing extending from the corresponding connector to an infusion site having an infusion site connector to deliver medicament to the infusion site. In some embodiments, connector 152 extending from cartridge 116 and the corresponding connector of the infusion set can be Luer Lock connections. Other infusion set configurations and attachments are described in U.S. Patent Publication No. 2014/0276423, which is hereby incorporated by reference in its entirety.

As depicted in the embodiment of FIGS. 4A-4B, pump system 100 can include a pump 102 and an infusion set 145. FIG. 4A depicts this infusion set 145 as not connected to pump while FIG. 4B depicts infusion set 145 connected to pump 102 via connectors 154 and 152. Infusion set 145 can include tubing 144 extending between a connector 154 and a site connector 146. Connector 154 can be configured to couple to pump 102 at connector 152. Site connector 146 can be configured to be attached to an infusion site on a user. The site connector 146 can attach or be pre-connected to a cannula and/or infusion needle that punctures the patient's skin at the infusion site. Various lengths of tubing 144 can be used in this embodiment to accommodate the user's preference.

Figure 5:
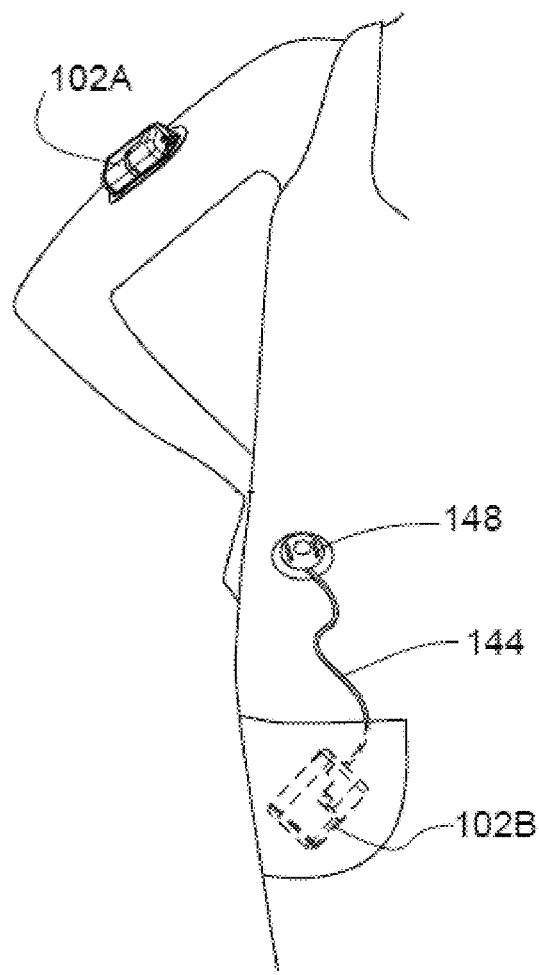
FIG. 5 depicts a schematic representation of a pump system according to an embodiment of the disclosure.

Referring to FIG. 5, in one embodiment a user can place the pump 102B in the user's pocket with infusion tubing 144 extending to an infusion set 148 on the user's body. Pump 102B can alternatively be carried by the user in other locations. Alternatively, the user can wear the pump 102A directly on the body. Such a pump 102A can include an adhesive patch that adheres to the skin and a cannula and/or infusion needle extending directly beneath the pump.

Figure 6A:
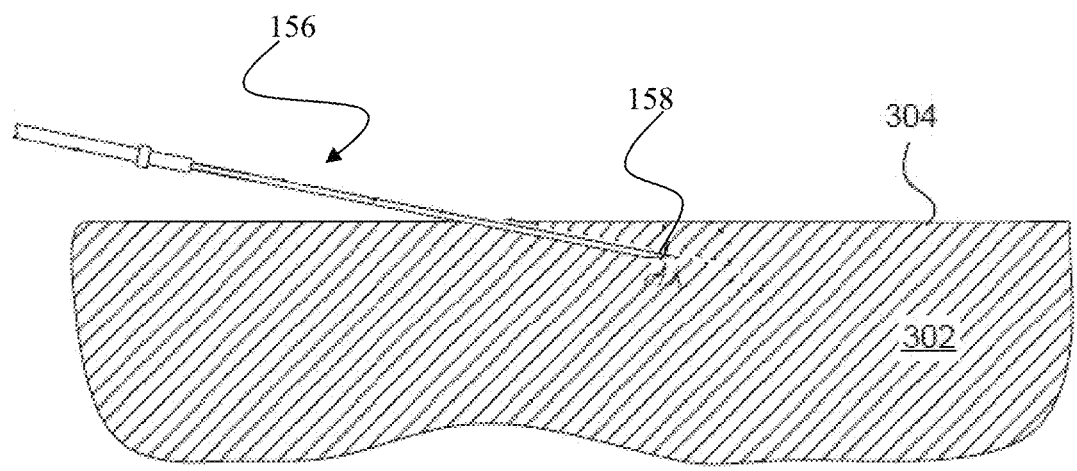
FIG. 6A depicts a schematic representation of a portion of an infusion set for use with an infusion pump according to an embodiment of the present invention inserted into a patient.
Figure 6B:
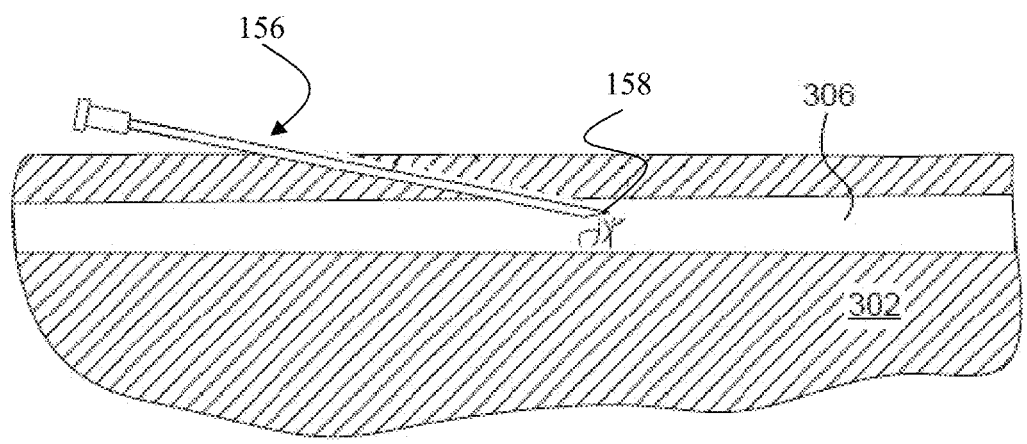
FIG. 6B depicts a schematic representation of a portion of an infusion set for use with an infusion pump according to an embodiment of the present invention inserted into a patient.

FIGS. 6A and 6B depict a cannula 156 of an infusion set such as described above inserted into a patient's body 302 at an insertion site. The cannula 156 can be inserted into a subcutaneous space under the patient's skin 304 as shown in FIG. 5A. Alternatively, the cannula 156 can be disposed within an inner lumen of a patient's fluid vessel 306, such as shown in FIG. 5B. The infusion set is in fluid communication with a dispense port of an infusion pump system, and fluids such as insulin and/or other suitable medicaments are shown being dispensed from an outlet port 158 of the cannula 156 and into the patient's body 302 at the insertion site.

As noted above, if a patient leaves the cannula inserted at the infusion site for too long a period of time, undesirable side effects such as infection and buildup of fat and scar tissue can result and patients are therefore instructed to rotate injection sites to avoid or minimize side effects. However, not all patients' bodies react the same to infusion therapy and not all infusion locations on a given patient will react the same, so time-based reminders set on the pump to instruct patients to rotate sites after a set amount of time are not ideal. Embodiments of the invention seek to maximize the effectiveness of insulin and other medicament therapy by utilizing CGM data to determine when a given infusion site is and is not viable such that the reminders to rotate infusion sites are tailored to the actual, specific site in use at a given time by a specific patient and not based on a set amount of time. Accordingly, a smart site change/reminder system can utilize CGM and/or BGM data to determine when a site should be rotated.

Figure 7:
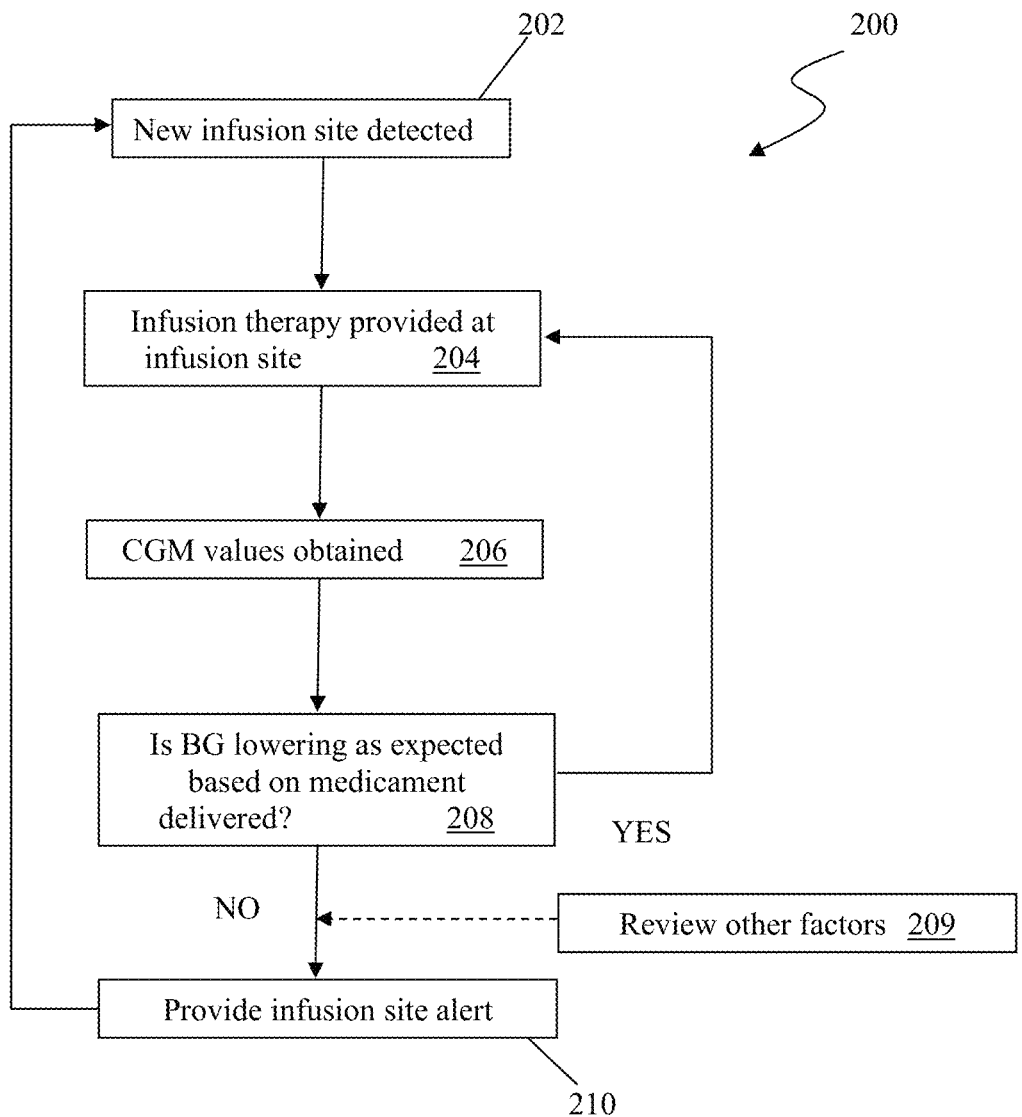
FIG. 7 depicts a flow chart of method steps for monitoring infusion sites according to an embodiment.

Referring to FIG. 7, a flowchart of method steps 200 taken by a smart site change/reminder system is depicted. Such a system can include an ambulatory infusion pump including an infusion set configured to be attached to the patient for delivery of medicament, a CGM and/or BGM configured to obtain glucose level readings of the patient, and, optionally, a remote control device for remotely controlling the pump such as a smartphone or dedicated remote controller. In some embodiments, pump may deliver medicament to the user through an infusion site directly beneath the patient, such as pump 102A in FIG. 5, rather than through an infusion set.

At step 202, the system detects that a new infusion site is being put into use. Use of a new infusion site can be detected by, for example, user input instructing the pump to fill the tubing and/or cannula with medicament as would be required when attaching a new infusion set to the pump. Infusion therapy is initiated and generally continuously provided at the infusion site as dictate by preprogrammed pump settings at step 204. While infusion therapy is ongoing, CGM values of the patient are obtained at step 206. The CGM values are monitored at step 208 to determine based on the amount and/or rate of medicament delivered if the user's glucose level is responding to the medicament, i.e., lowering, as expected. If the CGM data indicates that the user's glucose level is responding as expected, infusion therapy at the infusion site and CGM monitoring continues uninterrupted. If the CGM data indicates that the user's glucose level is not responding appropriately, it can indicate that insulin absorption at the site has been affected due to prolonged use of the site. The system can them provide an alert instructing and/or recommending that the user change infusion sites at step 210. After the infusion site alert has been provided and a new infusion site has been detected, the system can revert back to step 202.

Monitoring step 206 can be performed in any number of ways. For example, CGM data can be monitored in response to regular basal insulin delivery, after delivery of a meal or correction bolus, or a combination of both to determine if the user's glucose levels are responding as expected to the amount of medicament delivered in a given time period. Alternatively or additionally, an infusion site test bolus can be delivered periodically for the specific purpose of monitoring the body's response to the bolus to determine the validity of the infusion site. In various embodiments, monitoring can be conducted continuously or periodically, can begin as soon as a site is in use or after a predetermined time of use such as, for example after 1 or 2 days of use, and/or can be done at regular intervals or irregular intervals, such as for example, by increasing the frequency of monitoring the longer an infusion site has been in use. Monitoring step 206 can further take into account the lag time it takes for medicament such as insulin to be absorbed into the blood stream and affect blood glucose.

Determination step 208 can also be performed in any number of ways. For example, the determination can be made by monitoring a correction factor for the patient, i.e., how much a given amount (e.g., 1 unit) of insulin is lower the patient's blood glucose over a predetermined period of time (e.g., 2 to 4 hours). Most patients will have programmed a patient-specific correction factor into the device for use in calculating medicament deliveries such as correction boluses. Determination step 208 can therefore use the monitored glucose levels and medicament delivery amounts to calculate the actual effective correction factor for the patient over a given period of time and compare the effective correction factor to the stored patient correction factor. If the effective correction factor is lower than the stored patient correction factor by a predetermined amount such as, for example, 25%, 50%, etc., the infusion site alert can be provided. In other embodiments, additional or alternative parameters can be monitored at determination step 208, such as, for example, rate of change of glucose level, comparison of glucose levels to one or more thresholds, a frequency or amount of correction boluses, etc.

In some embodiments, the determination step 208 can take into account one or more additional factors in addition to the CGM data and amount of medicament delivered in order to ensure that an unexpected response is not due to some other factor than site loss at the infusion site. For example, if the user has indicated that a meal will be consumed by, for example, entering a carbohydrate value or based on a preprogrammed meal time, the medicament being delivered will not have the expected direct affect on the current glucose level because of the consumption of carbohydrates that the meal bolus is delivered to counteract. Exercise can also affect insulin absorption and glucose levels. If, for example, the user enters input indicating the user will be exercising, the user has a preprogrammed exercise time scheduled and/or an activity monitor detects that the user is exercising, an unexpected response may not be related to any issues with the infusion site. As such, method 200 can include an optional step 209 in which other factors that can affect glucose levels and/or insulin absorption can be reviewed and an alert may not be provided if the review finds other factors may be the cause.

In this manner, the systems and methods described herein provide an improvement over previous systems that dictate site rotations based on a predetermined time period. Use of CGM data for comparison of glucose levels to medicament delivered enables the system to determine when a site is no longer valid based on actual physiological data for the specific patient rather than on a preset estimated time period. In addition, the system enables an infusion site to be used for the entire period that the site is adequately absorbing medicament, rather than requiring a site rotation at an arbitrary cutoff point. Thus, in some embodiments, the system will not instruct the patient to rotate the infusion site until the glucose data indicates that the current infusion site no longer viable and not responding to the medicament as expected.

Figure 8:
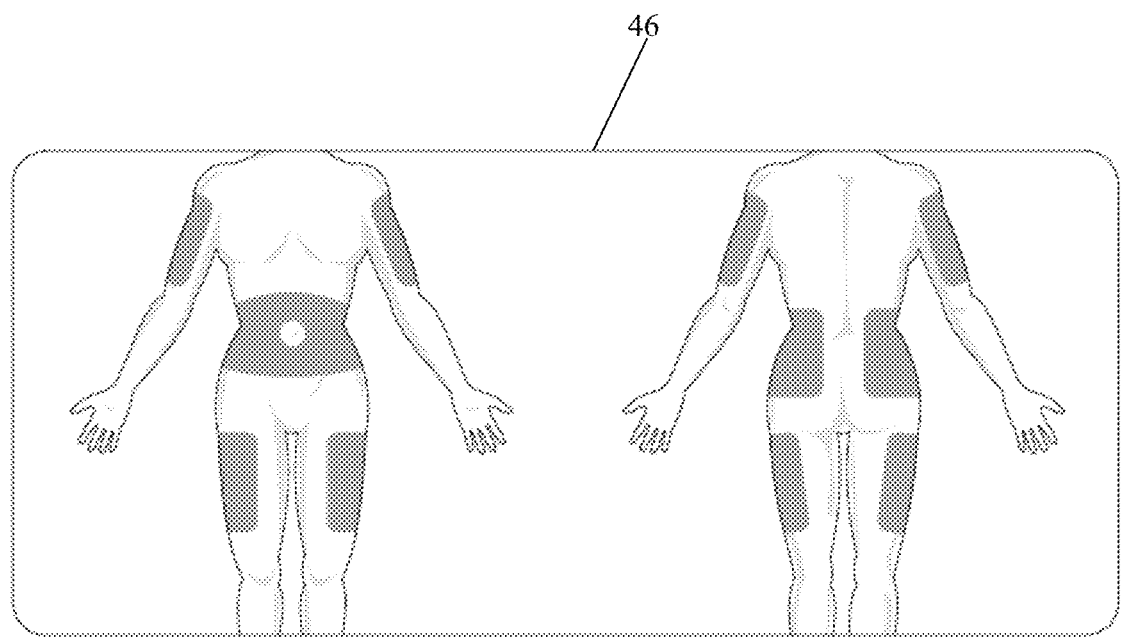
FIG. 8 depicts a user interface for use with an ambulatory infusion pump system according to an embodiment.

In some embodiments, the system can request and/or enable the user to enter a site location when a new infusion site is detected and track the effectiveness of various sites on the user's body with respect to other sites and/or over time. In various embodiments, the user can be presented with a graphic depiction of the body from which to select an infusion site, can be presented with a scrollable list of common infusion sites and/or can be presented with a text box for entering a name of an infusion site. FIG. 8 depicts one embodiment of a user interface 46 that could be presented on an infusion pump and/or remote control device to enable the user to select a region of the body to indicate where a new infusion set has been inserted. In the depicted embodiment, the user interface 46 displays both front and rear views of the body with the most commonly used infusion sites highlighted. In some embodiments, the user may only be able to select the highlighted regions while in others the highlighted regions may be provided only as a guide to the user or no regions may be highlighted. In some embodiments, the user may select a general area as depicted in FIG. 8 or may be able to zoom in by selecting a given area to indicate more accurately where in the area the infusion set has been inserted. Other inputs that the system may use in tracking infusion site effectiveness are type of insulin or other medicament used, type of infusion set used, etc.

Once the user has entered a given infusion site, the system can track various infusion parameters while the infusion site is in use. For example, the system can track how long the infusion site is used before it is rotated, which, in some embodiments can be based on CGM data as discussed above. The system can also track insulin delivery parameters and CGM data to determine the effectiveness of the site over time. Once data on a number of sites has been obtained, effectiveness of the various sites and/or how long various sites remain effective can be compared by the system and/or presented to the user to aid in future infusion site rotations.

In some embodiments, the system can provide recommendations along with a site rotation reminder or alert based on historical effectiveness of various sites. Similarly, the system can compare effectiveness of a given site over time based on multiple uses of the same site or sites in the same region of the body. Site rotation recommendations can further utilize this data to, for example, only recommend a given site location if the historical data of the location indicates that it has been long enough since the site has been used for the site to have regained a threshold level of effectiveness.

The effectiveness of a given infusion site can take into account various factors. For example, the CGM data and medicament delivery data can be used to calculate an effective correction factor for the site. In some embodiments, the effective correction factor can be compared to a stored patient correction factor and the effectiveness of the site determined, at least in part, based on that comparison. In embodiments, the system may only recommend and/or allow use of infusion sites that have been providing an effective correction factor equal to or greater than the stored patient correction factor, or within a certain range of the stored patient correction factor. The length of time for which a site remains valid over a given use or average over multiple uses can also factor into the effectiveness of the site. In some embodiments, the system may provide an average score based on the effective correction factor, the length of time the site has been used, and/or other factors for easy comparison of the effectiveness of each site, which may be continually updated each time a site is used. In addition to comparing the effectiveness of different sites, the data for each time a particular site is used can be compared to determine how often a site can be used and when a site is ready to be used again. For example, if a given site shows a decrease in effective correction factor when used again within, e.g., 3 days, but an effective correction factor equivalent with or greater than the stored patient correction factor when used again within, e.g., 4 days, the system can not recommend and/or prevent a patient from entering that site unless it has been at least 4 days since it has been used. Although the infusion pump embodiments herein are specifically described primarily with respect to the delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357,603; 10,357,606; 10,492,141. commonly owned U.S. Patent Publication Nos. 2009/0287180; 2012/0123230; 2013/0053816; 2014/0276423; 2014/0276569; 2014/0276570; 2017/0182248; 2017/0250971; 2018/0021514; 2018/0071454; 2019/0240398; 2019/0307952; and 2019/0365997 and commonly owned U.S. patent application Ser. Nos. 16/507,146 and 16/598,343.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A method of providing diabetes therapy to a patient with a portable infusion pump, comprising:
   detecting that a patient has inserted a cannula for delivery of medicament with the portable infusion pump at an infusion site on a body of the patient;
   delivering the medicament to the patient at the infusion site with the portable infusion pump;
   receiving data obtained by a glucose sensor;
   monitoring glucose levels of the patient based on the data obtained by the glucose sensor;
   determining, based on a stored correction factor of the patient, if the monitored glucose levels are lowering as expected in response to the medicament being delivered to the patient; and
   providing an infusion site alert to the patient if it is determined that the monitored glucose levels are not lowering as expected in response to the medicament.

2. The method of claim 1, wherein providing an infusion site alert includes instructing the patient to rotate to a new infusion site at a different location on the body.

3. The method of claim 2, further comprising not instructing the user to rotate to a new infusion site until it is determined that the monitored glucose levels are not lowering as expected in response to the medicament.

4. The method of claim 1, wherein detecting that the patient has inserted the cannula at the infusion site includes receiving user input instructing the portable infusion pump to fill the cannula with the medicament.

5. The method of claim 1, wherein detecting that the patient has inserted the cannula at the infusion site includes receiving user input instructing the portable infusion pump to fill tubing extending between the portable infusion pump and the cannula with the medicament.

6. The method of claim 1, wherein determining if the monitored glucose levels are lowering as expected in response to the medicament being delivered to the patient includes determining if the monitored glucose levels are lowering as expected in response to one or more of preprogrammed basal insulin delivery, meal boluses and correction boluses.

7. The method of claim 1, wherein determining if the monitored glucose levels are lowering as expected in response to the medicament being delivered to the patient includes determining if the monitored glucose levels are lowering as expected in response to a test bolus of insulin delivered to determine a response at the infusion site rather than in response to actual or anticipated increases in glucose levels.

8. The method of claim 1, wherein determining if the monitored glucose levels are lowering as expected in response to the medicament being delivered to the patient includes continuously monitoring glucose levels with respect to the medicament being delivered.

9. The method of claim 1, wherein determining if the monitored glucose levels are lowering as expected in response to the medicament being delivered to the patient includes periodically monitoring glucose levels with respect to the medicament being delivered at regular intervals.

10. The method of claim 1, further comprising reviewing other factors that could cause the monitored glucose levels to not lower as expected in response to the medicament being delivered to the patient prior to providing the infusion site alert.

11. The method of claim 10, wherein reviewing other factors includes determining if a meal has recently been consumed by the patient.

12. The method of claim 10, wherein reviewing other factors includes determining if the patient is exercising.

13. The method of claim 1, wherein determining if the monitored glucose levels are lowering as expected in response to the medicament being delivered to the patient based on a stored correction factor of the patient includes calculating an effective correction factor for the patient based on the monitored glucose levels and delivered medicament and comparing the effective correction factor to the stored correction factor.

14. The method of claim 1, determining if the monitored glucose levels are lowering as expected in response to the medicament being delivered to the patient based on a stored correction factor of the patient includes determining if an amount of insulin delivered over a predetermined period of time lowered the user's glucose level as expected in view of the stored correction factor.

15. A method of providing diabetes therapy to a patient with a portable infusion pump, comprising:
   detecting that a patient has inserted a cannula for delivery of medicament with the portable infusion pump at an infusion site on a body of the patient;

delivering the medicament to the patient at the infusion site with the portable infusion pump;

receiving data obtained by a glucose sensor;

monitoring glucose levels of the patient based on the data obtained by the glucose sensor;

determining if the monitored glucose levels are lowering as expected in response to the medicament being delivered to the patient including determining if an amount of insulin delivered over a predetermined period of time lowered the user's glucose level as expected in view of a predetermined correction factor for the patient; and providing an infusion site alert to the patient if it is determined that the monitored glucose levels are not lowering as expected in response to the medicament.

16. The method of claim 15, wherein determining if an amount of insulin delivered over a predetermined period of time lowered the user's glucose level as expected in view of the stored correction factor includes calculating an effective correction factor for the patient based on the amount of insulin and amount that the user's glucose level lowered and comparing the effective correction factor to the stored correction factor.

17. The method of claim 15, further comprising reviewing other factors that could cause the monitored glucose levels to not lower as expected in response to the medicament being delivered to the patient prior to providing the infusion site alert.

18. The method of claim 17, wherein reviewing other factors includes determining if a meal has recently been consumed by the patient.

19. The method of claim 17, wherein reviewing other factors includes determining if the patient is exercising.

* * * * *